United States Patent [19]
Vaughan

[11] Patent Number: 5,208,011
[45] Date of Patent: May 4, 1993

[54] ULTRAVIOLET RESISTANT SUNSCREEN COMPOSITIONS

[75] Inventor: Christopher D. Vaughan, Ft. Lauderdale, Fla.

[73] Assignee: Sun Pharmaceutical Corp., Pompano Beach, Fla.

[21] Appl. No.: 577,690

[22] Filed: Sep. 4, 1990

[51] Int. Cl.$^5$ .................... A61K 7/42; A61K 7/44; A61K 9/10; A61K 9/12
[52] U.S. Cl. .................... 424/59; 424/47; 424/60; 424/78.02; 424/78.03; 514/458; 514/781; 514/783; 514/937; 514/938
[58] Field of Search .................... 424/59, 60

[56] References Cited

U.S. PATENT DOCUMENTS

| | | | |
|---|---|---|---|
| 3,666,732 | 5/1972 | Skoultchi et al. | 260/78.5 BB |
| 3,751,563 | 8/1973 | Richardson | 424/60 |
| 4,254,104 | 3/1981 | Suzuki | 424/170 |
| 4,481,186 | 11/1984 | Deckner | 424/99 |
| 4,797,272 | 1/1989 | Linn et al. | 424/59 |

OTHER PUBLICATIONS

Abstract 100:194053w, Patent JP 59 16,534, Lion Corp.
Abstract 104:10390g, Patent JP 60,149,511, Lion Corp.
Abstract 104:226764e, Patent JP 61 00,300, Lion Corp.
Berger et al. "A Climatology of Sunburning Ultraviolet Radiation".
Scotto et al., "Biologically Effective Ultraviolet Radiation: Surface Measurements in the United States, 1974 to 1985", *Science Reports*, vol. 239, Feb. 12, 1988, pp. 726–763.
C.T.F.A International Cosmetic Ingredient Dictionary 95, 294, 316, 335, 506, 507, 587.
*Kirk–Othmer Encyclopedia of Chemical Technology*, 3rd edition, vol. 7, pp. 152–154.
"Sunscreen Drug Products for Over-The-Counter Human Drugs", Federal Register, Aug. 25, 1978, Part II.
*CRC Handbook of Solubility Parameters and Other Cohesion Parameters*, Chapter 2.1 of A. F. M. Barton, CRC Press, Inc., Boca Raton, Florida (19183).

Primary Examiner—Dale R. Ore
Attorney, Agent, or Firm—McAndrews, Held & Malloy, Ltd.

[57] ABSTRACT

A sunscreen composition for leaving a protective film on skin, comprising a UVB light absorbing sunscreen, a polymer vehicle, an oil-soluble solubilizer, and alkoxylated castor oil as an emulsifier. The protective film has an aggregate cohesive energy of from about 80 to about 150 calories per cc, preferably 100 to 115 calories/cc. The film is water resistant, unusually stable to UV radiation, nonirritating, and physically protective.

3 Claims, 1 Drawing Sheet

5,208,011

ULTRAVIOLET RESISTANT SUNSCREEN COMPOSITIONS

FIELD OF THE INVENTION

The present invention relates to sunscreen compositions for protecting skin against sunlight, and particularly to sunscreen compositions which have low water solubility, enhanced stability to solar radiation, and low irritation potential.

BACKGROUND OF THE INVENTION

Sunscreen compositions must fulfill a number of requirements to be effective. First, they must absorb the appropriate wavelengths of ultraviolet radiation to prevent sunburn and other forms of cellular damage and aging of the skin. Second, they must be stable, safe, and non-irritating to skin. Third, because sunscreen compositions are most often used for several hours at a time in bright sunlight, near water, or under conditions where perspiration is induced, the compositions must be resistant to water and ultraviolet (UV) light. A background on the contents and function of sunscreens is provided in *Kirk-Othmer Encyclopedia of Chemical Technology*, 3rd Ed., Vol. 7, pages 152 to 154, which is hereby incorporated herein by reference.

Many commercial sunscreen products and their ingredients are known to provide reduced protection after being in use for a period of time. Thus, protection is reduced precisely when it is most needed to counteract long exposure to sunlight. It is also known that dyes will photobleach under sunlight.

Many known sunscreen compositions are made water-resistant by combining an ultraviolet light absorbing active ingredient with a skin substantive resin as a vehicle. Such vehicles cover the active ingredient on the surface of the skin. The regulatory monograph "Sunscreen Drug Products For Over-The-Counter Human Drugs", published by the FDA in the *Federal Register* on Aug. 5, 1978, warns of the risk of occlusively driving the active ingredient into the skin, causing irritation or other toxic reactions. (This monograph is hereby incorporated by reference in its entirety herein.) Decomposition of active UV absorbers may produce irritating and otherwise unsafe by-products which likewise may be absorbed through the skin, and the irritation potential of some active ingredients themselves has recently been demonstrated.

The prior art teaches stable oil-in-water emulsions for cosmetic use. One of many emulsifiers suggested by the art for such emulsions is hydrogenated castor oil ethoxylated with 30 to 100 moles of ethylene oxide per mole of oil, combined with a water-soluble solvent. One of many known utilities for such emulsions is as a suntan preparation.

The prior art also discloses oil-in-water emulsions useful as skin lotions which contain a soap of glucamine and a fatty acid as a non-irritating emulsifying agent. One of many potential fatty acids is ricinoleic acid. Ricinoleic acid is derived from castor oil. One of many possible adjuvants mentioned in the prior art for use with the emulsions is a sunscreen.

Polyethoxylated castor oil has been disclosed to be useful as a solubilizer for liquid soap, as a skin moisturizer, and for degreasing pig skin.

SUMMARY OF THE INVENTION

One aspect of the present invention is a sunscreen emulsion having 1) an aqueous phase comprising water and 2) a water-insoluble phase comprising a UVB light-absorbing sunscreen, a polymer vehicle, an oil-soluble solubilizer, and alkoxylated castor oil. The emulsion has a high degree of resistance to degradation in sunlight, and thus maintains most of its potency against sunburn when worn in sunlight for an extended period. The present emulsion is non-irritating and prevents absorption of the active sunscreen ingredients into the skin. The present composition is also waterproof, losing little activity when the wearer perspires or swims.

Another aspect of the present invention is a sunscreen film comprising an ultraviolet light absorbing sunscreen, a polymer, a solubilizer, and alkoxylated castor oil. The sunscreen film of the present invention provides an initial sun protection factor (SPF) when applied to skin. After the film is exposed to intense sunlight for four hours, the residual protection provided by the film is at least about 70% of the initial SPF. The sunscreen film also provides residual protection corresponding to at least 80% of its initial SPF after immersion in either fresh or salt water for four hours. The sunscreen films of the present invention are nonirritating to skin.

DETAILED DESCRIPTION OF PREFERRED EMBODIMENTS

Figure 1:
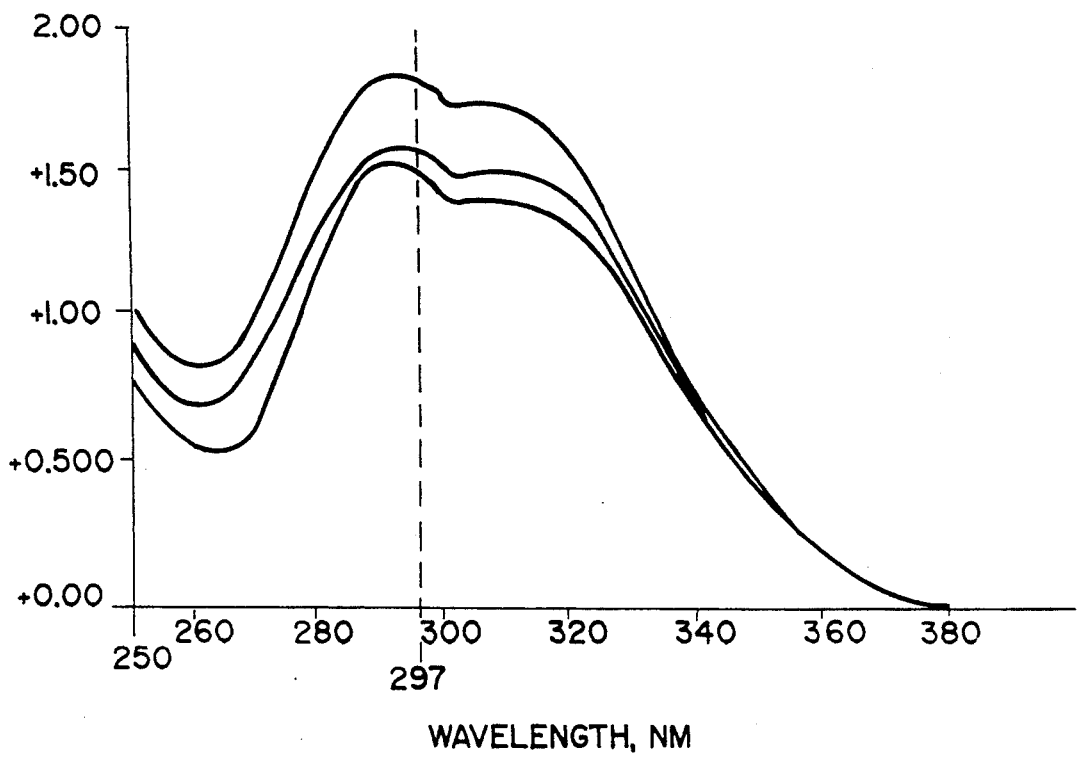
FIG. 1 shows UV absorbance on the y-axis (wherein "2.0" at the top of the scale represents 99% absorption) versus wavelength on the X-axis for a film having the composition of Example 4. The three plots show the absorption of UVB light by the composition after exposure to intense natural sunlight for zero hours (top curve), two hours (middle curve), and four hours (bottom curve).

The sunscreen composition of the present invention is an emulsion including 1) an aqueous phase comprising water and 2) a water-insoluble phase comprising a UV light-absorbing sunscreen, a polymer, an oil-soluble solubilizer, and alkoxylated castor oil. The composition is long-lasting, durable, and stable under normal use. The sunscreen resists degradation by sunlight and removal by water, yet is not irritating to skin.

The sunscreen emulsions of the present invention comprise from about 35% to about 96%, preferably from about 55% to about 85%, of an aqueous phase and from about 4% to about 65%, preferably from about 15% to about 45%, of a water insoluble phase. In the present disclosure, the percentage of any adjuvant or phase is based on the weight of the entire composition. The present emulsions contain the water insoluble phase and the aqueous phase in amounts effective to provide a stable emulsion having activity as a sunscreen. Either phase may be the outer phase of the emulsion within the scope of the present invention, but in the preferred embodiment the aqueous phase is the outer phase.

Some ingredients predominantly reside in the aqueous phase, other ingredients predominantly reside in the water insoluble phase, still other ingredients reside in the interface between the phases, and some ingredients are partitioned between the two phases or are found in an additional phase of the present emulsion. Thus, an indication herein that an ingredient resides in a certain phase is not an exclusion of that ingredient from other phases of the present emulsions.

Aqueous Phase

The aqueous phase predominantly comprises water. The aqueous phase may further comprise one or more adjuvants, constituting from 0% by weight to about 50% by weight of the emulsion. One adjuvant useful herein is a water dispersible plant extract such as aloe vera gel. Water dispersible preservatives are useful herein as adjuvants in the aqueous phase. The emulsions preferably contain from about 0.1% to about 1.0% of one or more water dispersible preservatives. Exemplary water dispersible preservatives include methylparaben and imidazolidinyl urea. Other preservatives may be used as well. The aqueous phase may contain water dispersible fragrances, preferably as from 0% to about 1% of the composition. Other water dispersible additives, such as water dispersible colors and dyes, are also contemplated herein.

Water-insoluble Phase

The water insoluble phase comprises an ultraviolet light absorbing sunscreen, a polymer, an alkoxylated castor oil, and an oil-soluble solubilizer, and may further comprise various adjuvants.

The compositions contemplated herein comprise from about 1% by weight to about 50% by weight, preferably from about 1% to about 33% by weight, of sunscreen-active ingredients. The present composition may desirably contain opaque sunscreens, such as zinc oxide or titanium dioxide, which function by providing an opaque barrier to UV light. The preferred compositions contain one or more of the following sunscreens, which function by selectively absorbing ultraviolet light having wavelengths of from about 290 to about 320 nanometers (the UVB wavelengths which are responsible for tanning or burning skin):

octocrylene
2-ethylhexyl salicylate;
2-ethoxyethyl-p-methoxycinnamate;
2-ethylhexyl-p-methoxycinnamate (also known as octyl methoxycinnamate);
2-[bis(2-hydroxyethyl)-amino]ethyl salicylate;
hydroxyethylaminoethyl-p-methoxycinnamate;
pentyl 4-dimethylaminobenzoate;
2-hydroxy-1,4-naphthoquinone;
3,3,5-trimethylcyclohexyl salicylate;
2-ethylhexyl-2-cyano-3,3-diphenyl acrylate;
ethyl 4-[bis(2-hydroxypropyl)amino]benzoate;
digalloyl trioleate;
methyl anthranilate;
salicylic acid 3,3,5-trimethyl ester (commonly known as homomenthyl salicylate or homosalate);
glyceryl-p-aminobenzoate;
p-aminobenzoic acid;
isobutyl-p-aminobenzoate;
isoamyl-p-dimethylaminobenzoate;
2-hydroxy-4-methoxybenzophenone-5-sulfonic acid;
2-phenylbenzimidazole-5-sulfonic acid;
2-2-dihydroxy-4-methoxybenzophenone;
2-hydroxy-4-methoxybenzophenone (commonly called oxybenzone);
4-mono(3-hydroxypropyl)amino isomer of ethyl benzoate;
4-bis(3-hydroxypropyl)amino isomer of ethyl benzoate;
red petrolatum;
2-ethylhexyl-p-dimethylaminobenzoate; and
mixtures thereof.

The sunscreens listed above are the sunscreens now approved as safe and effective for human use by the United States Food and Drug Administration. New sunscreens which may be discovered in the future may also be used within the scope of the present invention.

The sunscreens preferred herein are selected from the group consisting of:
oxybenzone;
2-ethoxyethyl-p-methoxycinnamate;
2-ethylhexyl salicylate;
homosalate;
octocrylene;
titanium dioxide; and
mixtures thereof.

Water-insoluble film-forming polymers are added to the composition to provide a matrix or binder which physically envelops the sunscreen with the aid of the oil-soluble solubilizer, preventing the sunscreen from being absorbed by the skin. The polymers also prevent the sunscreen from being rubbed off by physical contact with clothing, towels, furniture, other parts of the body (e.g. scratching the protected area), etc.

While the present invention is not limited by the accuracy of the following theory as to its mode of operation, the inventors contemplate that preventing absorption of the sunscreen keeps the sunscreen between the sun and the protected skin, thus maximizing its ability to absorb damaging UVB radiation. The inventors further contemplate that preventing absorption of the sunscreen active ingredient by the wearer's skin also reduces the potential of the sunscreen or its products of light induced decomposition to irritate or sensitize the skin of the wearer. The present sunscreens are thus believed to function differently than compositions which are intended to occlude the sunscreen active ingredient against the skin or to cause it to be absorbed into the skin.

Specific polymers contemplated for use herein include the following:
aliphatic alkenes, for example, polyethylene, oxidized polyethylene, polybutene, polypropylene, or their copolymers;
copolymers of vinyl chloride and maleic acid or anhydride;
alkyl polyvinyl pyrrolidones, such as copolymers of polyvinyl pyrrolidone with eicosene or dodecene;
acrylic resins;
methacrylic resins; and
mixtures thereof.

Each said polymer can have a carbon chain length of from about 50 to about 5000 carbon atoms.

Other polymers contemplated for use herein are those mentioned in U.S. Pat. Nos. 3,666,732 (polymers of p-aminobenzoic acid and its derivatives, and their copolymers with acrylic, methacrylic, itaconic, or crotonic acids, alkyl esters, and hydroxyalkyl esters); 3,666,732 (polyalkene resins); and 3,751,563 (polyalkene resins). The disclosures of polymers in the U.S. patents listed in the preceding sentence are hereby incorporated herein by reference. Other water-insoluble polymers which have utility in skin-contacting cosmetics are also contemplated for use herein. The present compositions preferably contain from about 1.5% to about 12.5% of one or more such polymers.

The water insoluble phase of the present emulsion further comprises at least one oil-soluble solubilizer having a cohesive energy between about 80 and about 150 calories per cc., preferably from about 100 to about 115 calories per cc. The aggregate cohesive energy of all the oil-soluble solubilizers used in a particular composition is also preferably from about 100 to about 115 calories per cc. The cohesive energy of a material is defined in Chapter 2.1 of A. F. M. Barton, *CRC Handbook of Solubility Parameters and Other Cohesion Parameters*, CRC Press, Inc., Boca Raton, Fla. (19183). The composition preferably contains from about 0.1% to about 15% of such solubilizers. Oil-soluble solubilizers give the present sunscreen compositions, and particularly the films resulting from their application, a greater affinity for skin. Oil-soluble solubilizers also function as plasticizers for the polymer vehicles described above, so the film of the sunscreen composition will be mobile enough to form a thin layer on the wearer's skin and flexible enough to conform closely to the wearer's skin during use.

Specific oil-soluble solubilizers contemplated herein include the following:
aliphatic lactates of fatty acids having from about 12 to 20 carbon atoms, for example, myristyl lactate;
Guerbet alcohols;
fatty alcohols;
dialkyl maleates;
alkyl ricinoleates;
alkyl hydroxystearates;
alkyl acetyl ricinoleates;
nonionic surfactants having HLB's between 1 and about 5;
alkyl salicylates such as octyl salicylate;
and mixtures thereof.

("Alkyl" is defined herein generally to include straight or branched chain alkyl having from 1 to about 22 carbon atoms.) Exemplary nonionic surfactants useful herein include lanolin alcohols, glycerol monooleate, and sorbitan esters of fatty acids (such as sorbitan stearate and sorbitan oleate).

Another necessary ingredient of the water insoluble phase is from about 0.1 to about 10% by weight of alkoxylated castor oil, more broadly defined as consisting essentially of alkoxylated ricinolein. From 1 to 100 moles of an alkylene oxide (preferably ethylene oxide), preferably from about 5 to about 40 moles of ethylene oxide, may be combined with each molecule of ricinolein. Mixtures of alkoxylated castor oils having different amounts or kinds of alkylene oxide content are also contemplated for use herein.

The water-insoluble phase of the present composition may also contain various adjuvants. From about 0.1% to about 5% of a fatty alcohol having from 6 to 22 carbon atoms, such as stearyl alcohol or a mixture of fatty alcohols, may be added to the water insoluble phase to make a creamier product. For a pump sprayable or aerosol product, the viscosity of the composition may be reduced by using less or no fatty alcohol. Preservatives dispersible in the water insoluble phase can be used; an example is propyl paraben. Antioxidants such as tocopherol may be used in the water insoluble phase. Propellants may be blended into the composition to facilitate delivery of the sunscreen in aerosol form, using conventional aerosol technology.

Complete Emulsion

Various ingredients may be added after the emulsion is formed. Typically, these are ingredients dispersible in the outer phase, which in the preferred embodiment is the aqueous phase.

The emulsion can contain levelling agents, which are ingredients dispersed in the emulsion to assist the application of a uniform film of the composition on the skin. From 0 to about 5%, preferably from 0 to about 3.5%, of the composition may be a levelling agent. Exemplary levelling agents are silica, clays or earths, titanium dioxide, mica, and zinc oxide. The levelling agent can also be added in larger amounts to function as an opaque barrier layer.

Some other adjuvants which may be employed are counterirritants such as allantoin, plant extracts, vitamins, etc.

The sunscreen emulsion of the present invention preferably has a pH between about 3.5 and about 6.5, so it will be compatible with human skin, but is not limited to this pH range.

Sunscreen Films

Another aspect of the invention is a sunscreen film comprising the nonvolatile ingredients of an emulsion as previously described, applied to human skin. The film may be prepared by forming a sunscreen emulsion as previously described, applying a coating of the emulsion on skin or another substrate, and drying the emulsion sufficiently to essentially remove the water from the composition (primarily by evaporation). The film may also be applied by dispersing the ingredients of the desired film in a solvent to form a lacquer or gel, applying a coating of the lacquer or gel, and drying or otherwise removing the solvent.

The sunscreen film provides an initial SPF when it is first applied. The initial SPF is defined herein as the ratio of (1) the increment of time treated skin can remain in the sun, to (2) the increment of time untreated sun can remain in sun of equal intensity with the same effect (tanning or burning). "Initial SPF" is defined herein identically to "SPF" or "sun protection factor", measured as prescribed by the FDA in the monograph cited above. The desired initial SPF typically lies between 2 (for products designed to moisturize and minimally protect already-tanned skin) and 30 or more (for sunscreens meant to virtually eliminate the effects of sun on extremely sensitive skin).

The present invention is not limited to any particular initial SPF, though it has the greatest benefit when used to formulate a composition having a high initial SPF and intended for extended use. The initial SPF of a formulation can readily be modified by using more or less of the active ingredient in the emulsion. This may be accomplished by varying the proportion of the active ingredient in the nonaqueous phase, varying the ratio of the aqueous phase to the nonaqueous phase, or selecting a more or less potent active ingredient or combination of ingredients.

"Residual protection" is defined herein as the ratio of (1) the increment of time treated skin can remain in the sun after the sunscreen film has been exposed to a defined adverse environmental condition, to (2) the increment of time untreated skin can remain in sunlight of equal intensity with the same effect (tanning or burning). One defined adverse environmental condition is exposure of a sunscreen film to intense sunlight having a flux of about 51 mJ/cm²/hr for four hours. Flux in the UVB range is measured with a Sunburning Ultraviolet (S.U.V.) meter sold by Solar Light Co., Philadelphia, Pa. Another defined adverse environmental condition is immersion of a film of the composition in fresh or salt water for four hours. "Residual protection" is not a term defined by the FDA, and takes into account the attenuation of sunscreen efficacy after exposure to sunlight and/or water. Initial SPF does not take this attenuation into account, as it is measured without previously aging the sunscreen film in intense sunlight. The ratio of residual protection to initial SPF is a measure of the degree to which a sunscreen preparation retains its activity after exposure to the indicated adverse environmental condition.

The present sunscreen film provides residual protection for the skin supporting it, after exposure to sunlight having a flux of about 51 mJ/cm²/hr for four hours, which is at least about 70%, preferably at least about 80%, most preferably at least about 85%, of its initial SPF. The film is thus highly resistant to attenuation of its protection by exposure to sunlight.

The present sunscreen film provides residual protection for the skin supporting it, after immersion of the skin and film in fresh or salt water for four hours, which is at least about 90%, preferably at least about 95%, most preferably at least about 98%, of its initial SPF. The film is thus resistant to attenuation of its initial protection due to extended exposure to water.

The present sunscreen film is particularly resistant to the combined effects of water and sunlight. The present film provides residual protection of at least about 40%, preferably at least about 55%, more preferably at least about 70%, still more preferably at least about 80%, and most preferably at least about 90% of its initial SPF after four hours' exposure to water as defined above, followed by three hours' exposure to sunlight having a UVB flux of 51 mJ/cm²/hr.

Although highly water and sunlight resistant, and thus potentially present on the skin for many hours at a time, the film of the present invention is substantially nonirritating to the skin. The sunscreen film can be removed from the skin easily by washing with soap and water.

The sunscreen film preferably has a cohesive energy between about 80 and about 150 calories per cc, more preferably between about 100 and 115 calories per cc.

The cohesive energy of the film determines its affinity for human skin. Untreated skin has a cohesive energy of about 100 to about 115 calories per cc. The closer the cohesive energy of the sunscreen film is to the cohesive energy of skin, the more readily the film will adhere to the skin. The cohesive energy of the film can be modified by incorporating solubilizers in the emulsion or other film-forming composition.

EXAMPLES

Several exemplary sunscreen compositions according to the present invention are given in Table 1 below. The compositions were prepared by blending the ingredients of the water-insoluble phase at a temperature high enough to maintain the water insoluble phase in molten form, separately dispersing the ingredients of the aqueous phase in deionized water, and homogenizing the aqueous and nonaqueous phases together at a temperature at which both phases are liquids. Levellers (if used) and in some instances other ingredients were added after the emulsion was formed.

Compositions made according to the present invention were tested for decomposition resistance, for water or washing resistance, and for any tendency to irritate skin.

The decomposition resistance of Example 4 of Table I was measured as follows. A film of the sunscreen was applied approximately 2 mg/cm² thick on a slide made of polyvinylidene chloride film, and the initial UVB absorption spectrum (having a wavelength between 290 and about 320 nanometers) of the slide was measured. The slide was then laid flat and exposed to intense South Florida sunlight having a UVB flux of about 51 mJ/cm²/hr between 11 AM and 3 PM under a clear sky in October. The slide was exposed for one hour. The slide was then reinserted in the UV spectrophotometer and its UVB absorption spectrum was again recorded. The slide was exposed to sunlight for three more one hour periods. After each period the UVB absorption spectrum was again recorded. These spectra were used to calculate the residual protection provided by the films. The initial and two residual absorbance spectra of the sunscreen film made from the composition of Example 4 are superimposed in FIG. 1. The relative areas under the plots between the critical UVB wavelengths of about 290 to about 320 nanometers indicate the degree of sunburn and skin cancer protection provided by the respective samples.

The FDA SPF test method taken from the monograph cited above, involving actual exposure of human skin treated with the composition to sunlight, was also carried out for Example 4.

FIG. 1 first shows that the freshly-applied film of Example 4 according to the present invention absorbed all but about 1/15th of the incident radiation within the UVB range before it was exposed to sunlight, measured according to the spectrophotometric test method identified above. The film had an SPF of about 15.79 as determined by the FDA method, thus validating the spectrophotometer method. Second, degradation of the film's sunscreen activity after a one-hour exposure to intense sunlight was only about 11.2%, to a residual protection of about 14.0, and the additional degradation after a total of four hours' exposure to intense sunlight was only about 7.6% more, leaving a residual protection of about 12.8. Thus, the composition maintained over 80% of its efficacy after long exposure to intense sunlight.

The composition of Example 1 according to the present invention was similarly tested for resistance to degradation in intense sunlight. Its initial SPF was 16.13, as measured by the FDA method. Its residual protection after four hours' exposure to intense sunlight having a UVB flux of about 51 mJ/cm²/hr was about 11.2, representing 71% of its original activity.

Figure 2:
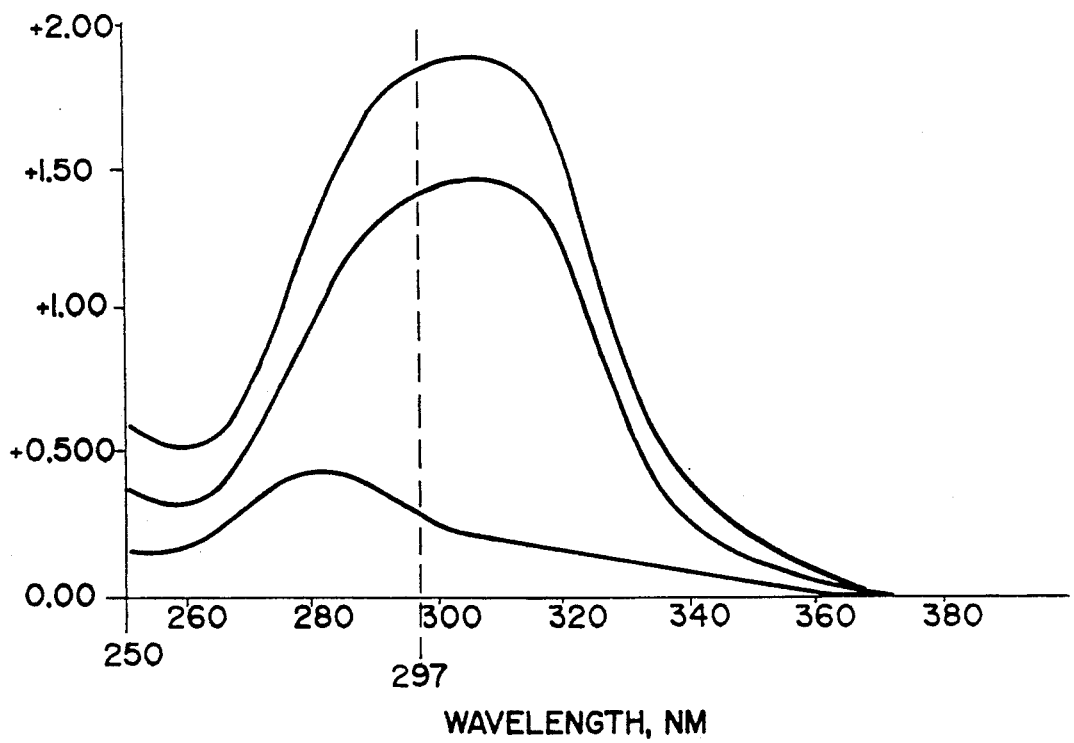
FIG. 2 is similar to FIG. 1, except that the sunscreen film tested was formed by applying a commercially available composition representing the prior art.

To compare the results obtained in Examples 1 and 4 to those provided by current commercial sunscreens, the same spectrophotometric decomposition resistance test was performed on four nationally distributed, brand name suntan lotions. FIG. 2 shows that the market leading composition tested here initially effectively absorbed the UVB wavelengths. About 95%, or all but 1/20th, of the incident UVB light was absorbed. The initial SPF was also claimed to be about 20 by the manufacturer. However, the composition degraded substantially upon exposure to intense sunlight. After one hour of exposure to intense sunlight it provided residual protection of about 15.3, representing 23.6% degradation. After four hours' exposure to intense sunlight, the same product provided a residual protection SPF of about 3.4, representing about 83.2% degradation of its efficacy as a sunscreen. Thus, this originally highly effective sunscreen had little of its original activity after exposure to intense sunlight for an extended time.

Another of the commercially marketed sunscreens tested, which claimed an SPF of 30+ and is marketed as a sunscreen for infants, lost 48.1% of its initial activity after two hours and a total of 54.9% of its initial activity after four hours.

Yet another of the commercial sunscreens claimed an SPF of 15 and claimed "four hour protection". This sunscreen lost 34.3% of its initial activity after two hours' exposure to intense sunlight and 37.1% of its initial activity after four hours' exposure to intense sunlight.

The washing or water immersion resistance of the present invention was tested as follows. A film of each composition tested was applied to slides and initially tested for UVB absorption in the manner described previously. Each slide was then immersed in a container of water for four hours. The slides were removed, allowed to dry in air, and retested for UVB absorption. The reduction in UVB absorption, expressed as a percentage, was reported as percent wash-off. Using this method, performance of the composition of Example 1 was compared to that of three commercial products; the result is shown in Table II below. The composition of Example 1 hardly washed off at all (only about 4%), while the commercial compositions washed off to a far greater degree (up to 23%). Then the films were subjected to intense sunlight for three hours to simulate real use conditions of exposure to both sunlight and water. The UVB absorption of the residual films was measured as previously described. The residual protection after washing and exposure to intense sunlight is recorded in Table II, the right-hand column. The composition of Example 1 was shown to be far superior to other tested compositions after exposure to washing and intense sunlight.

The skin irritation potential of the composition of Example 4 was tested on 50 human subjects by putting two drops of the composition on the skin of a subject, covering the treated skin with a semioccluded, hypoallergenic patch, and leaving it covered and unwashed for 24 hours. Then the patch was removed and the presence or absence of a reaction determined. After a rest period of 24 hours the test was repeated on the same part of the subject's skin. Ten consecutive patch tests were conducted on each subject in this manner. Ten to 14 days later, the test was repeated one final time. No irritation was noted after any of the patch tests in this study.

The composition of Example 4 has a low enough viscosity to be mixed with a propellant and applied as an aerosol spray. The composition of Example 5 has a low enough viscosity to be applied from a pump spray bottle.

While the invention has been described in connection with the preferred embodiment, it is not intended to limit the invention to the particular form set forth above, but on the contrary, it is intended to cover such alternatives, modifications and equivalents as may be included within the spirit of the invention as defined by the appended claims.

TABLE I

| Example: | 1 | 2 | 3 | 4 | 5 |
|---|---|---|---|---|---|
| Non-aqueous Phase | | | | | |
| (% of emulsion wt.) | | | | | |
| Octyl methoxycinnamate | 5.25 | 3.50 | 7.71 | 5.00 | 7.00 |
| Stearic acid | 4.84 | 4.84 | 4.85 | 0.25 | 0.25 |
| Oxybenzone | 3.40 | 2.30 | 5.91 | 3.20 | 4.50 |
| Octyl salicylate | 3.00 | 2.00 | 5.15 | 2.90 | 4.00 |
| Isodecyl nonanoate | — | — | — | 3.00 | 3.00 |
| Polyethylene | 2.15 | 1.61 | 2.13 | — | — |
| Octyl maleic copolymer | — | — | — | 2.00 | 2.05 |
| Stearyl alcohol | 1.61 | 2.42 | 2.57 | — | — |
| Glyceryl stearate | 1.55 | 1.50 | 1.54 | — | — |
| PEG-40 Castor Oil | 1.25 | 1.30 | 1.34 | 1.75 | 1.75 |
| PEG-5 Castor oil | — | — | — | 0.25 | 0.25 |
| Methyl acetyl ricinoleate | 1.00 | 1.00 | 3.09 | 2.00 | 2.00 |
| Coconut oil | — | — | — | 0.80 | 0.80 |
| Myristyl lactate | 0.25 | 0.25 | 0.26 | — | — |
| Cetyl alcohol | — | — | — | 0.12 | 0.12 |
| Dimethicone | 0.10 | 0.10 | 0.10 | — | — |
| PEG-7 Glyceryl cocoate | 0.10 | 0.10 | 0.10 | — | — |
| Propyl paraben | 0.10 | 0.10 | 0.10 | 0.15 | 0.15 |
| Tocopherol | 0.01 | 0.01 | 0.01 | — | — |
| Tocopheryl acetate | — | — | — | 0.10 | 0.10 |
| BHA | — | — | — | 0.01 | 0.01 |
| Cocoa butter | — | — | — | 0.01 | 0.01 |
| Example: | | | | | |
| Aqueous Phase | | | | | |
| (% of emulsion wt.) | | | | | |
| Deionized water | 70.87 | 74.75 | 59.62 | 60.46 | 56.04 |
| Magnesium-aluminum silicate | 0.75 | 0.75 | 0.88 | — | — |
| Hydroxyethylcellulose | 0.30 | — | 0.48 | — | — |
| Methyl paraben | 0.25 | 0.25 | 0.26 | .15 | .15 |
| EDTA | 0.05 | 0.05 | 0.05 | — | — |
| Hydrolyzed collagen | 0.01 | 0.01 | 0.01 | — | — |
| Aloe vera gel | 2.00 | 2.00 | 2.47 | 16.00 | 16.00 |
| Silica | 0.48 | 0.48 | 0.50 | — | — |
| PEG 45 M (1% aqueous) | — | — | — | 0.50 | 0.50 |
| Sorbitol | — | — | — | 0.50 | 0.50 |
| Glycerine | — | — | — | 0.50 | 0.50 |
| Preservative | 0.50 | 0.50 | 0.62 | 0.30 | 0.30 |
| Triethanolamine | 0.18 | 0.18 | 0.25 | — | — |
| Fragrance | — | — | — | 0.05 | 0.02 |
| Total Weight | 100.00 | 100.00 | 100.00 | 100.00 | 100.00 |
| Sun Protection Factor | 16 | 10 | 25 | 15 | 20 |

TABLE II

SPRAY-ON SUNSCREEN LOTIONS

| Sunscreen | Initial SPF | Wash-off (%) | Residual Protection After Wash-off and 3 Hours' Sunlight (%) |
|---|---|---|---|
| Example 1 | 15 | 4% | 92% |
| Market Leader | 20 | 23% | 15% |
| Next Nat'l Brand | 15 | 17% | 35.4% |
| Next Nat'l Brand | 20 | 8% | 15.4% |

What is claimed is:

1. A sunscreen emulsion composition comprising:
   A. from about 1% to about 50% by weight of a sunscreen selected from the group consisting of:
      octyl methoxycinnamate,
      oxybenzone
      octyl salicylate, and
      combinations thereof;
   B. from about 1.5% to about 12.5% by weight of a film-forming polymer having a carbon chain length of from about 50 to about 5000 carbon atoms, said polymer being selected from the group consisting of:
polyethylene,
an octyl maleic copolymer, and
combinations thereof;
C. from about 0.1% to about 15% by weight of an oil-soluble solubilizer selected from the group consisting of:
stearyl alcohol,
glyceryl stearate,
methyl acetyl ricinoleate,
myristyl lactate,
PEG-7 glyceryl cocoate, and
combinations thereof;
D. from about 0.1% to about 10% by weight of ethoxylated castor oil having an average of from about 1 to about 100 moles of ethylene oxide moieties per mole of castor oil; and
E. from about 35% to about 96% by weight water.

2. The sunscreen emulsion composition of claim 1, comprising: from about 1% to about 33% by weight of said sunscreen and from about 55% to about 85% by weight of said water, wherein said ethoxylated castor oil has an average of from about 5 to about 40 moles of ethylene oxide moieties per mole of castor oil.

3. The sunscreen emulsion composition of claim 2, comprising:
A. from about 11% to about 12% by weight of said sunscreen;
B. about 2% by weight of said film-forming polymer;
C. about 5% by weight of said oil-soluble solubilizer;
D. from about 1% to about 2% by weight of said ethoxylated castor oil; and
E. from about 60% to about 71% by weight of said water.

* * * * *

UNITED STATES PATENT AND TRADEMARK OFFICE
CERTIFICATE OF CORRECTION

PATENT NO. : 5,208,011

DATED : May 4, 1993

INVENTOR(S) : Christopher D. Vaughan

It is certified that error appears in the above-identified patent and that said Letters Patent is hereby corrected as shown below:

Cover sheet, References Cited under Other Publications
after Abstract 104:226764e, Patent JP 61 00,300, Lion Corp. insert --

Chem. Abstract 1986, Vol. 104: 10391h, Patent JP 60,149,516
Chem. Abstract, 1986, Vol. 104:10392j, JP60, 149,516 --.

Signed and Sealed this

Twenty-seventh Day of December, 1994

Attest:

BRUCE LEHMAN

*Attesting Officer*   *Commissioner of Patents and Trademarks*